United States Patent [19]

McCombie

[11] 4,435,413

[45] Mar. 6, 1984

[54] (5R-6S,8R)-6-(1-HYDROXYETHYL)-2-(2-GLYCYLAMINOETHYLTHIO)-PENEM-3-CARBOXYLIC ACID

[75] Inventor: Stuart W. McCombie, West Orange, N.J.

[73] Assignee: Schering Corporation, Kenilworth, N.J.

[21] Appl. No.: 461,845

[22] Filed: Jan. 28, 1983

[51] Int. Cl.[3] .................. A61K 31/425; C07D 499/00
[52] U.S. Cl. ............................. 424/270; 260/245.2 R
[58] Field of Search ................. 260/245.2 R; 424/270

[56] References Cited

U.S. PATENT DOCUMENTS 4,260,618 4/1981 Christensen et al. ............ 424/270 X

FOREIGN PATENT DOCUMENTS 55-153789 11/1980 Japan.
2013674 8/1979 United Kingdom.

*Primary Examiner*—Natalie Trousof
*Assistant Examiner*—Vera C. Clarke
*Attorney, Agent, or Firm*—Gerald S. Rosen; Bruce M. Eisen

[57] ABSTRACT

There is disclosed the antibacterial 5R,6S,8R-6-(1-hydroxyethyl)-2-(2-glycylaminoethylthio)penem-3-carboxylic acid, its pharmaceutically acceptable salts and esters as well as compositions containing them and methods for their use.

12 Claims, No Drawings

(5R-6S,8R)-6-(1-HYDROXYETHYL)-2-(2-GLYCYLAMINOETHYLTHIO)-PENEM-3-CARBOXYLIC ACID

BACKGROUND OF THE INVENTION

This invention relates to (5R,6S,8R)-6-(1-hydroxyethyl)-2-(2-glycylaminoethylthio)-penem-3-carboxylic acid and its pharmaceutically acceptable salts and esters, which compounds possess potent antibacterial activity.

There is a continuing need for new antibacterial agents because continued extensive use of effective antibacterials gives rise to resistant strains of pathogens.

SUMMARY OF THE INVENTION 5R,6S,8R-6-(1-hydroxyethyl)-2-(2-glycylaminoethylthio)-penem-3-carboxylic acid and its pharmaceutically acceptable salts and esters possess antibacterial activity against both gram-positive and gram-negative bacteria.

DETAILED DESCRIPTION

When tested in standardized microbiological assays, the compounds of this invention are active against such gram-positive organisms as *Staphylococcus aureus* and *Bacillus subtilis,* and such gram-negative organisms as *E. coli* and Salmonella, at test levels of 0.1 to 2.0 micrograms/ml. Additionally, they show activity against organisms which product beta-lactamases, e.g., penicillinase and cephalosporinase, indicating a resistance against these enzymes. For instance, the sodium salt of 5R,6S,8R-6-(1-hydroxyethyl)-2-(2-glycylaminoethylthio)-penem-3-carboxylic acid is active against *Staphylococcus aureus* 76070105 at a test level of 0.5 microgram/ml. When tested against *E. coli* 71120101 (a beta-lactamase producing organism) the compound exhibits activity at 1.0 microgram/ml.

The compounds of this invention exhibit low protein binding and their metabolites have little or no unpleasant odor.

As antibacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g., transdermal. Parenteral administration is preferred. Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; nonionic, cationic and anionic surfactants; ethylene glycol polymers; betacyclodextrin; fatty alcohols; hydrolyzed cereal solids; water; polyalkylene glycols; gums; and petrolatum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, i.e., the age and weight of the individual being treated, the mode of administration, and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

As used herein, "pharmaceutically acceptable salts" means alkali metal salts such as sodium and potassium salts; alkaline earth metal salts such as calcium, magnesium and aluminum salts; amine salts formed from a wide variety of suitable organic amines, i.e., aliphatic, cycloaliphatic, (cyloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperidine. Acid addition salts formed from mineral acids such as hydrochloric, hydrobromic, hydroiodic, phosphoric or sulfuric acids, or formed from organic carboxylic or sulfonic acids such as trifluoroacetic, para-toluene sulfonic, maleic, acetic, citric, oxalic, succinic, benzoic, tartaric, fumaric, mandelic, ascorbic and malic acids. The compounds of this invention contain a 3-carboxylic group and a basic group (the amino group) which form an inner salt, i.e., a Zwitterion.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. For example, salts of the compound can be formed by treating with metal compounds such as alkali metal salts of suitable carboxylic acids, or with ammonia or a suitable organic amine, wherein preferably stoichiometric amounts or only a small-excess of the salt-forming agent is used. Acid addition salts of the compound are obtained in the usual manner, for example, by treating with an acid or a suitable anion exchange reagent. Inner salts of the compounds of formula, i.e., a zwitterion, may be formed by neutralizing salts such as acid addition salts to the isoelectric point. The esters are preparable in a manner analogous to the preparation of the corresponding esters of penicillins and cephalosporins.

Salts may be converted in the usual manner into the free carboxy compounds.

The compounds of this invention are prepared from allyl (5R,6S,8R)-2-(ethylthio)-6-(1-hydroxyethyl)-penem-3-carboxylate (whose preparation is described in European Patent application 8081004.41 published July 23, 1980 as number 0013662) via activation to the sulfoxide and displacement at the 2-position with 2-(N-allyloxycarbonylglycylamino)-ethanethiol followed by removal of the allyl groups.

The following examples illustrate the preparation of the compound and compositions of this invention.

EXAMPLE 1

Allyl-(5R,6S,8R,2'RS)-2-(Ethanesulfinyl)-6-(1-Hydroxyethyl)Penem-3-Carboxylate

Stir a solution of allyl-(5R,6S,8R,2'RS)-2-(ethanethio)-6-(1-hydroxyethyl)penem-3-carboxylate (31.5 g) in ethyl acetate (200 ml) and dichloromethane (100 ml) at 0°–5° C. Add a solution of m-chloroperoxybenzoic acid (80–85%; 22 g) in ethyl acetate (120 ml) over 0.5 hour. After a further 0.5 hour, add the solution to a stirred mixture of ethyl acetate (150 ml), water (125 ml) and sodium bicarbonate (15 g) and stir rapidly for 15 minutes. Dry the organic phase over NgSO$_4$, evaporate and chromatograph rapidly on silica gel, eluting 1:1 hexane-ethyl acetate then pure ethyl acetate. Evaporate the product fractions and pump the residue at high vacuum to give the title compound as a thick yellow oil.

PMR(CDCl$_3$): δ 1.2–1.6 (m,6H), 3.0–3.35 (m,2H), 3.38 (br.s, 1H, exch by D$_2$O), 3.83 (m, 1H), 4.18 (m, 1H), 4.75 (br.d, J=6.5 Hz), 5.2–5.6 (m,2H), 5.73 and 5.89 (both d, J-1.5 Hz, total 1H) and 5.8–6.2 (m, 1H).

The compound obtained is a mixture of isomers diastereoisomeric at the oxidized sulfur. The mixture was used as such in the next step since both isomers react.

EXAMPLE 2

2-(N-Allyloxycarbonylglycylamino)-Ethanethiol

Add pivaloyl chloride (2.4 ml) in CH$_2$Cl$_2$ (10 ml) to a cooled (0°–5° C.) and stirred solution of N-allyloxycarbonylglycine (3.18 g) and triethylamine (2.8 ml) in dry CH$_2$Cl$_2$ (50 ml). Stir the mixture at 0°–5° C. for 15 mins. and then add a solution of 2-aminoethanethiol hydrochloride (2.4 g) and triethylamine (2.8 ml) in ethanol (15 ml) and CH$_2$Cl$_2$ (40 ml). Stir at room temperature for 1 hour, wash the mixture with aqueous 2 N-H$_2$SO$_4$ and aqueous NaHCO$_3$, dry and evaporate. Triturate the resulting solid with ether, filter and dry to give the title compound.

PMR (CDCl$_3$): δ 1.42 (t, J=8 Hz, exch. by D$_2$O 1H), 2.61 (m, 2H), 3.50 (q, J=7 Hz, 2H), 3.88 (d, J=7 Hz, 2H), 4.57 (m, 2H), 5.1–5.5 (m, 2H), 5.6–6.2 (m, 2H; 1H exch. by D$_2$O) and 7.0 (br. S, 1H, exch by D$_2$O).

EXAMPLE 3

Allyl-(5R,6S,8R)-6-(1-Hydroxyethyl)-2-(2-[N-Allyloxycarbonylglycylamino]Ethylthio)Penem-3-Carboxylate Stir a solution of the product of Example 1 (0.50 g) and the product of Example 2 (0.58 g) at 0°–5° C. in dichloromethane and add thereto diisopropylethylamine (0.2 g). After 5 mins. wash the solution with 10% aqueous tartaric acid, dry and evaporate and purify the residue by preparative TLC (eluting with EtOAc; product Rf∼0.4) to obtain the title compound as a pale yellow foam.

PMR (CDCl$_3$): δ 1.35 (d, J=7 Hz, 3H), 3.16 (m, 2H), 3.4–4.0 (m, 6H), 4.24 (m, 1H), 4.60 (d, J=7.5 Hz, 2H), 4.63 (m, 2H), 5.2–5.6 (m, 4H), 5.75 (d, J=1.5 Hz, 1H), 5.7–6.2 (m, 3H) and 7.20 (br. t, J=7 Hz).

EXAMPLE 4

(5R,6S,8R)-6-(1-Hydroxyethyl)-2-(2-Glycylaminoethylthio)Penem-3-Carboxylic Acid

Stir a mixture of the product of Example 3 (0.225 g), 2-ethylhexanoic acid (0.20 g) and triphenylphosphine (0.05 g) at 30°–35° C. in CH$_2$Cl$_2$ (20 ml) under nitrogen and add thereto tetrakis(triphenylphosphine)palladium (0.03 g). After 1.5 h, collect the precipitate by centrifugation after adding ether (15 ml), wash with 3×10 ml of 4:1 Ether:CH$_2$Cl$_2$ and dry under nitrogen to give the title compound as a cream powder.

IR (nujol): 3400, 1770, 1650 and 1590 cm$^{-1}$.

In the following examples, the Active Ingredient is (5R,6S,8R)-6-(1-hydroxyethyl)-2-(2-glycylaminoethylthio)penem-3-carboxylic acid and an equivalent amount of any of its pharmaceutically acceptable salts and esters.

EXAMPLE 5

| No. | Ingredient | Capsules mg/capsule | mg/capsule |
|---|---|---|---|
| 1. | Active ingredient | 250 | 500 |
| 2. | Lactose USP | 100 | 50 |
| 3. | Corn Starch, Food Grade | 50 | 43.5 |
| 4. | Microcrystalline Cellulose NF | 95 | 50 |
| 5. | Magnesium Stearate NF | 5 | 6.5 |
|  | Total | 500 | 650 |

Method of Manufacture

Mix Items Nos. 1, 2, 3 and 4 in a suitable mixer for 10–15 minutes. Add Item No. 5 and mix for 1–3 minutes. Fill the mixture into suitable two-piece hard gelatin capsules using encapsulating machine.

EXAMPLE 6

| No. | Ingredient | Tablets mg/capsule | mg/capsule |
|---|---|---|---|
| 1. | Active ingredient | 250 | 500 |
| 2. | Lactose USP | 57 | 114 |
| 3. | Corn Starch, Food Grade, as a 10% paste in Purified Water | 20 | 40 |
| 4. | Corn Starch, Food Grade | 18 | 39 |
| 5. | Magnesium Stearate NF | 5 | 7 |
|  | Total | 350 | 700 |

Method of Manufacture

Mix Items Nos. 1 and 2 in a suitable mixer for 10–15 minutes. Granulate the mixture with Item No. 3. Paste wet granulation through a coarse screen (e.g., ¼″) if needed, and dry the wet granules. Mill the dried granules. Combine Item No. 4 and the dried granules and mix for 10–15 minutes. Add Item No. 5 and mix for 1–3 minutes. Compress the mixture to appropriate size and weight on a suitable tablet machine.

EXAMPLE 7

| Injectable Powder: (per vial) | | |
| --- | --- | --- |
| | g/vial | g/vial |
| Active Ingredient | 0.5 | 1.0 |

Add sterile water for injection or bacteriostatic water for injection for reconstitution.

EXAMPLE 8

| | Injectable Solution | |
| --- | --- | --- |
| Ingredient | mg/ml | mg/ml |
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°–70° C.
2. Cool to 25.35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22 membrane and fill into appropriate containers.
6. Terminally sterilize the units by autoclaving.

EXAMPLE 9

| Injectable Powder: (per vial) | |
| --- | --- |
| | g/vial |
| Active Ingredient | 1.0 |
| Sodium Citrate | 1.05 | pH is adjusted to 6.2 using 0.1 N citric acid solution.
Add sterile water for injection or bacteriostatic water for injection for reconstitution.

I claim:
1. (5R,6S,8R)-2-6-(1-hydroxyethyl)-2-(2-glycylaminoethylthio)penem-3-carboxylic acid and the pharmaceutically acceptable salts and esters thereof.
2. The compound of claim 1 wherein the pharmaceutically acceptable salt is an alkali metal salt.
3. The compound of claim 1 wherein the pharmaceutically acceptable salt is an alkaline earth metal salt.
4. The compound of claim 1 wherein the pharmaceutically acceptable salt is an amine salt.
5. The compound of claim 1 wherein the pharmaceutically acceptable salt is an acid addition salt.
6. The compound of claim 1 wherein the pharmaceutically acceptable esters are metabolizable esters.
7. The compound of claim 2 wherein the alkali metal is sodium.
8. An antibacterially effective pharmaceutical composition comprising an antibacterial effective amount of a compound of claim 1 in admixture with a pharmaceutically acceptable carrier therefor.
9. A method of treating or preventing susceptible bacterial infections which comprises administering to a host in need of such treatment or prevention a compound of claim 1 or a pharmaceutical composition thereof in an amount sufficient to treat or prevent such infection.
10. A method according to claim 9 wherein the route of administration is oral.
11. A method according to claim 9 wherein the route of administration is parenteral.
12. A method according to claim 9 wherein the route of administration is topical.

* * * * *